United States Patent [19]
Fujita et al.

[11] Patent Number: 5,385,823
[45] Date of Patent: Jan. 31, 1995

[54] METHOD FOR ASSAYING NUCLEIC ACIDS AND PROTEINS USING ANTHRACENE DERIVATIVE PHOSPHATE

[75] Inventors: Satoshi Fujita; Masayoshi Momiyama; Naoto Kagiyama; Yasumitsu Kondo; Hiroshi Hori, all of Sapporo, Japan

[73] Assignee: Aisin Seiki Kabushiki Kaisha, Kariya, Japan

[21] Appl. No.: 994,727

[22] Filed: Dec. 22, 1992

[30] Foreign Application Priority Data

Dec. 27, 1991 [JP] Japan .................................. 3-347019
May 8, 1992 [JP] Japan .................................. 4-115640

[51] Int. Cl.6 .................. C12Q 1/68; C12Q 1/42; G01N 33/533
[52] U.S. Cl. ............................. 435/6; 435/7.1; 435/21
[58] Field of Search .......................... 435/6, 21, 7.1

[56] References Cited

U.S. PATENT DOCUMENTS

4,978,614 12/1990 Bronstein .................. 435/21

FOREIGN PATENT DOCUMENTS

4114131 11/1991 Germany .

OTHER PUBLICATIONS

Vaughan et al., *Analytical Chemistry* 43(6), 721–724 (1971).
Schroeder et al., *BioEngineering* 5(3–4), 24–30 (1989), (Abstract).
Schmeer et al., *J. Clin. Microbiol.* 26(12), 2520–2525 (1988).
Coutlee et al., *J. Clin. Microbiol.* 27(5), 1002–1007 (1989).
"A Comparison of Chemiluminescent and Colorimetric Substrates in a Hepatitis B Virus DNA Hybridization Assay", by Irena Bronstein et al., *Annalytical Biochemistry*, vol. 180:95–98 (1989).
"A Fluorescent Detection Method for DNA Hybridization Using 2-Hydroxy-3-Naphthoic Acid-2'-Phenylanilide Phosphate as a Substrate For Alkaline Phosphatase", by Naoto Kagiyama et al., *Acta Histochem. Cytochem.*, vol. 25, No. 4, pp. 467–471, (1992).
"Non-radioactive Labeling and Detection of Nucleic Acids", by Christopher Kessler et al., *Bio. Chem. Hoppe Seyler*, vol. 371, pp. 917–927, (Oct. 1990).

*Primary Examiner*—Margaret Parr
*Assistant Examiner*—Kenneth R. Horlick
*Attorney, Agent, or Firm*—Burns, Doane, Swecker & Mathis

[57] ABSTRACT

Method for assaying nucleic acids and proteins employing no radiosotope labeling, which is suitable for data storage and allows to carry out the detection efficiently and high sensitivity. The sample selectable from the group of nucleic acids, proteins, and other chemical compounds is adhered on a nylon membrane filter to be bound to a phosphatase. Then the phosphatase is reacted with an anthracene derivative phosphate followed by irradiating the reaction product with ultraviolet light to detect a fluorescence emitted therefrom.

4 Claims, 4 Drawing Sheets

| Examples | Anilines | Compounds |
|---|---|---|
| 7 | 2-biphenylaniline | 3-Hydroxy-N-(2,2'-triphenyl)-2-anthracenecarboxamide phosphate |
| 8 | 2-methyl-4-bromoaniline | 3-Hydroxy-N-1'-methyl-3-bromophenyl-2-anthracenecarboxamide phosphate |

FIG. 3

METHOD FOR ASSAYING NUCLEIC ACIDS AND PROTEINS USING ANTHRACENE DERIVATIVE PHOSPHATE

BACKGROUND OF THE INVENTION

Field of the Invention

The present invention relates to an efficient method for assaying nucleic acids and proteins by fluorescence.

Description of the Related Arts

The medical and biological fields have increasingly employed the methods for detecting the nucleic acids. Such method have been used in various fields, i.e., clinical medicine field for hereditary disease diagnosis and virus inspection; breeding field for breeding qualification, and seeds appraisal; and forensic medicine field for determining paternity and criminal investigation.

Such assaying methods, in general utilize a labeled probe, for example, a DNA (or RNA) probe which is labeled with a radioactive isotope, hybridizing the labeled probe with a target nucleic acid and then detecting the target nucleic acid by autoradiography However, hybridization methods which utilize radioactive isotypes comprise many drawbacks which pose serious obstacles to further application and development of this technology.

The drawbacks of hybridization methods which use radioactive isotope labels are as follows.

(a) In nucleic acid hybridization, the method lacks any spatial resolution sufficient to reveal relative positional relationship between contiguous signal.

(b) Experimental procedures using isotope can be only carried out in isotope laboratories equipped with special facilities. This is a cause for hindering application of the hybridization method especially for clinical diagnosis.

(c) Use of isotope is dangerous for laboratory workers even in laboratories. In addition, a danger for ordinary people always exists because of wastes, and the like.

(d) A long time (several weeks to several months) may be required for detection, so the use of such methods for rapid clinical diagnosis is difficult.

(e) Radioactivity decays with a definite half-life period so that experiments should be scheduled to fit a purchase date of isotope. If the schedule chart is slightly altered, there would be a danger of wasting isotope or experimental results in a large scale.

(f) In order to enhance detection sensitivity, it is required to incorporate radioactivity to a nucleic acid probe as high as possible. However, the nucleic acid labeled enough to increase its radioactivity easily suffers from radioactive disintegration.

(g) In general, radioactive isotypes are extremely expensive. This prevents further use of such hybridization methods.

In view of such background, some DNA or RNA labeling method in place of radioactive isotope have been developed.

For example, Japan Patent Application Laid Open No. 215300/1989 discloses Digoxigenin labeling method developed by the company named Boehringer Mannheim. This method employs alkaline phosphatase as enzyme, and BCIP/NBT (5-bromo-4-chloro-3-indolyl phosphate/Nitroblue tetrazolium chloride) as its substrate. PCT Patent WO 88/00695 discloses the use of AMPPD (4-Methoxy-4-(3-phosphatephenyl) spiro(1,2-dioxetane-3,2'-adamantane) developed by Tropix Co., as the substrate of the alkaline phosphatase. This method with the aid of chemical emission has contributed to reduce the detection period.

Both sensitivities of the above two methods are lower than that of RI (radio isotope) labeling method. However, they are sufficiently high to facilitate the use of such methods.

In the former method (hereinafter referred to as BCIP/NBT method) for detecting the weak signal by color development, it is difficult to take a picture of the signal to be stored as clear data. Since the signals on a nylon membrane filter gets discolored over time, they may not last six months at longest. In the above aspect, this method is not suitable for data storage.

The latter method (hereinafter referred to as AMPPD method) overcomes the disadvantage of BCIP/NBT method as described above, i.e., data storage, and contributes to reduce the detection period. The resolution of this method, however, is substantially inferior to that of the former method. In instances wherein the detected signal amounts varies in a wide range, plural samples should be prepared by executing detection two or more times with each condition varied for synthetic judgment. Such work requires well-experienced technique and sufficient time. Since this method employs X-ray film, the result cannot be obtained until it is photosensitized, resulting in poor operability.

SUMMARY OF THE INVENTION

It is an object of the present invention to provide a method for assaying nucleic acids and protein employing no RI labeling method, which has an excellent operability as well as allowing to store the data and to execute detection with high sensitivity.

The present invention is characterized to provide the method for assaying a sample selected from the group consisting of nucleic acids, proteins and chemical compounds which comprises the steps of binding the sample to phosphatase, reacting the phosphatase with an anthracene derivative phosphate, irradiating the reaction product with an excited light, and detecting an emitted fluorescence.

The anthracene derivative phosphate is expressed by a general formula of P-An-B-R, where "P" represents the phosphate bound to the third C of cyclic part of anthracene, "An" represents the cyclic part of anthracene, "B" represents a binding group for binding the second C of the cyclic part of anthracene to "R", and the "R" represents an aromatic group bound to the binding group.

The binding group designated as "B" is an amide binding group. The aromatic group designated as "R" is benzene cyclic part having groups of methyl, dimethyl, methoxy, dimethoxy, phenyl, diphenyl, bromo, and chloro. The anthracene derivative phosphate is expressed by the following chemical formulas from 1 to 16.

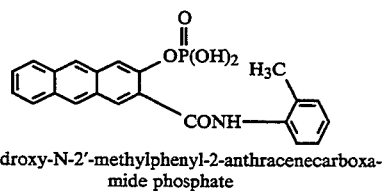

Formula 1

3-Hydroxy-N-2'-methylphenyl-2-anthracenecarboxamide phosphate

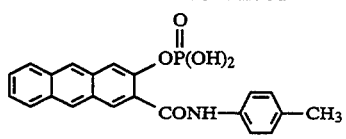

3-Hydroxy-N-4'-methylphenyl-2-anthracenecarboxamide phosphate

Formula 2

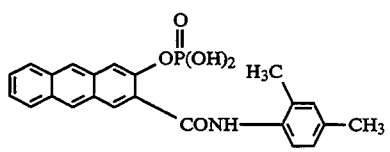

3-Hydroxy-N-2',4'-dimethylphenyl-2-anthracenecarboxamide phosphate

Formula 3

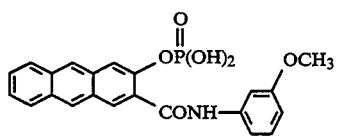

3-Hydroxy-N-3'-methoxyphenyl-2-anthracenecarboxamide phosphate

Formula 4

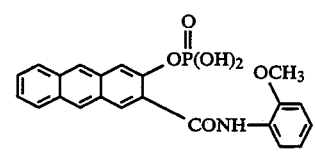

3-Hydroxy-N-2'-methoxyphenyl-2-anthracenecarboxamide phosphate

Formula 5

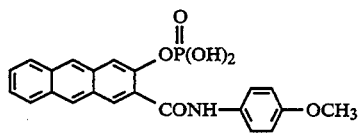

3-Hydroxy-N-4'-methoxyphenyl-2-anthracenecarboxamide phosphate

Formula 6

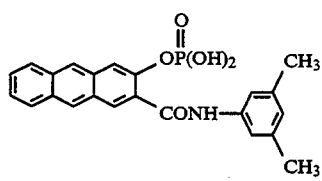

3-Hydroxy-N-3',5'-dimetylphenyl-2-anthracenecarboxamide phosphate

Formula 7

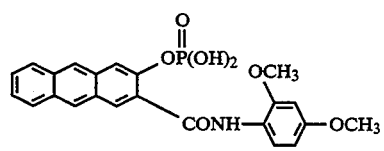

3-Hydroxy-N-2',4'-dimethoxyphenyl-2-anthracenecarboxamide phosphate

Formula 8

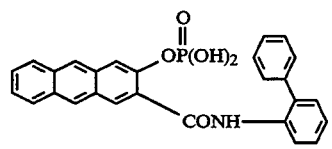

3-Hydroxy-N-2'biphenyl-2-anthracenecarboxamide phosphate

Formula 9

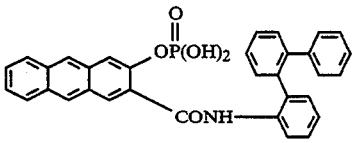

3-Hydroxy-N-(2,2'-triphenyl)-2-anthracenecarboxamide phosphate

Formula 10

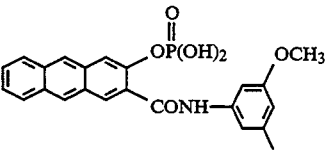

3-Hydroxy-N-3',5'-dimethoxyphenyl-2-anthracenecarboxamide phosphate

Formula 11

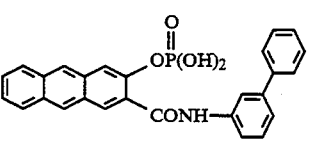

3-Hydroxy-N-3'-biphenyl-2-anthracenecarboxamide phosphate

Formula 12

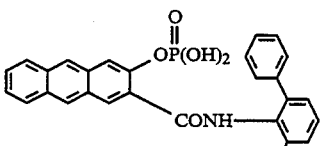

3-Hydroxy-N-2',6'-triphenyl-2-anthracenecarboxamide phosphate

Formula 13

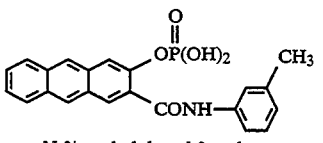

3-Hydroxy-N-3'-methylphenyl-2-anthracenecarboxamide phosphate

Formula 14

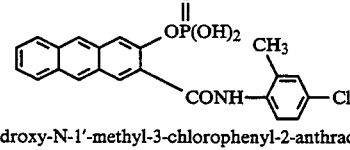

3-Hydroxy-N-1'-methyl-3-chlorophenyl-2-anthracenecarboxamide phosphate

Formula 15

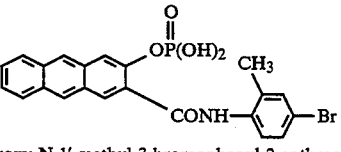

3-Hydroxy-N-1'-methyl-3-bromophenyl-2-anthracenecarboxamide phosphate

Formula 16

Other features and advantages of this invention will be apparent from the following description and the accompanying drawings.

BRIEF DESCRIPTION OF THE DRAWINGS

FIGS. 1–3 show anilines used for anthracene derivative phosphate and the same obtained in Examples 1 thru 8, respectively.

DETAILED DESCRIPTION OF THE INVENTION

Figure 1:
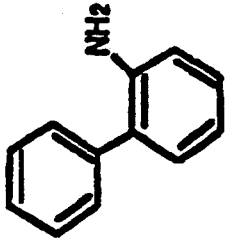

In the assaying method according to the present invention, anthracene derivative phosphate is reacted with the phosphatase followed by irradiating the reaction product with an excited light. As a result, dephosphorize form of the anthracene derivative phosphate emits fluorescence to be detected.

The phosphatase is bound to the sample, for example, nucleic acid, on the nylon membrane filter. The phosphatase, then, is reacted with the anthracene derivative phosphate to have fluorescent property and dephosphorize form thereof which is depositable to the nylon membrane filter. It is irradiated with the excited light for detecting the resultant fluorescence and its pattern by means of spot or electrophoretic band.

In the present invention, intense fluorescence can be obtained by using the anthracene derivative phosphate so that the detection sensitivity is improved. As a result, even a very small amount of DNA, $10^{-14}$g (10 fg), is detectable. In addition, the present invention requires no isotope, thus eliminating aforementioned problems caused by the use of isotope, resulting in safe environment.

In the conventional BCIP/NBT method, the data is judged by color identification. Accordingly taking the picture of the data may prevent such judgment. Moreover, the pictured signal gets discolored for about six months, resulting in difficulties of storing data. While the present invention employs fluorescent emission to eliminate the above drawbacks of the conventional method. So the pictured data can be clearly identified, allowing to store the data easily.

In the AMPPD method, the data cannot be obtained until the X-ray film is photosensitized. While in the present invention, the results of the experiment, whether it fails or not, can be seen even in the course of the experiment. Such excellent operability of the present invention may allow to confirm the progress of the experiment while continuing the experimental work.

The fluorescent wavelength range of phosphate modified fluorescence (450–600 nm) i.e., anthracene derivative phosphate of the present invention is longer than that of natural fluorescence (−400 nm) of the nucleic acid carrier membrane filter. Its fluorescence is so tense to eliminate the wavelength of the nucleic acid membrane filter spectroscopically, resulting in improving S/N ratio.

The anthracene derivative phosphate is absorbed effectively and rapidly to the nucleic acid carrier membrane filter immediately after the reaction with enzyme, and becomes insoluble to water. The resolution, thus, can be improved.

EXAMPLES

EXAMPLE 1

Experiment 1

According to Tetrahedron Vol. 11, pp. 133, (1960), 5.6 g (0.03 mol) of cyanuric chloride was dissolved in 150 ml of acetone. Then 10 g (0.03 mol) of the commercial 3-hydroxy-N-2-methyl phenyl anthracenecarboxamide (produced by SIGMA CHECMIKAL CO., NAPHTHOL AS-GR as trademark) was added to the solution. It was not dissolved completely, resulting in suspension.

The mixture was stirred very hard with a magnetic stirrer. The 24 ml(0.06 mol) of 10% NaOH solution was dropped to the mixture at the internal temperature kept in the range from 0° to 5° C. After adding 500 ml of NaOH solution and stirring for 1.5 hours, it turned to be the reddish brown solution. The 500 ml of 2% NaOH solution was further added to form yellow insoluble residue. The solution was heated to 60° C. and stirred so that the crystal dissolved gradually to terminate the reaction for 4 hours in total.

The reaction solution was cooled to the room temperature to remove the acetone by reducing pressure.

Then the insoluble residue was removed by reducing pressure and filtrating. The concentrated hydrochloric acid was added to the water tank with a great care to render strong acidic so that yellow insoluble residue was formed. It was extracted by ethyl acetate three times by using a separating funnel with the capacity of 2 l. The organic layer was washed in saturated salt water twice until it became neutral.

The organic layer was dehydrated by magnesium sulfate. The magnesium sulfate was removed by filtration. The ethyl acetate was also removed by reducing pressure, by which orange crystal was obtained. The thus obtained rough crystal was recrystalized with dimethyl formamide to obtain 3 g of 3-hydroxy-2-anthracene carboxamide as shown in the following formula (17). The chemical compound has its infrared absorption spectrum of 1684 cm$^{-1}$.

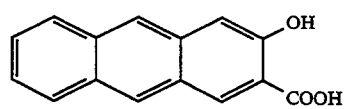

Formula 17

Experiment 2

According to the Reference Enzyme Histochemmistry, in a nitrogen atmosphere, 2 g (8.4×10$^{-3}$ mol) of 2-hydroxy-3-anthracenecarboxamide, and 30 ml of dehydrated xylene, and 1.28 g (7.6×10$^{-3}$ mol) of 2-phenylaniline were mixed in 100 ml flask equipped with Dimroth cooler to be stirred for 10 minutes at 80° C. The phosphorus trichloride (2.8×10$^{-3}$ mol) was added to the mixture to be heated and refluxed for 2 hours. The hot reaction solution was subjected to decantation to take supernatant liquid.

It was cooled to 4° C. to obtain precipitates by reducing pressure and filtrating. The crystal was washed in xylene and water. It was added to 3% HCl solution to be heated for 10 minutes. The hot solution was subjected to pressure reduction and filtration. The precipitate was further washed in hot water to be dried. The thus obtained crystal was recrystalized by using dimethylformamide and methanol (1:1) to obtain 520 mg of 3-hydroxy-2-anthracene carboxamide 2-phenylanilide as shown in the following formula (18).

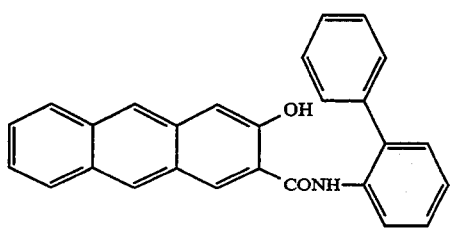

Formula 18

Experiment 3

In a nitrogen atmosphere, 520 mg ($1.34 \times 10^{-3}$ mol) of 3-hydroxy-2-anthracenecarboxamide-2-phenylanilide was dissolved in 5 ml of dehydrated pyridine to be stirred for 30 minutes at 0° C. The cooled phosphorus oxychloride ($3.3 \times 10^{-3}$ mol) was added to the mixture to be stirred for 4 hours at 0° C. The ice was added to terminate the reaction. The reacted mixture was purified with reversed-phase silica gel chromatographpy to obtain 320 mg of 3-hydroxy-2-anthracene carboxamide-2-phenyl anilide phosphate as shown in the following formula (9), resulting in the yield of 60%.

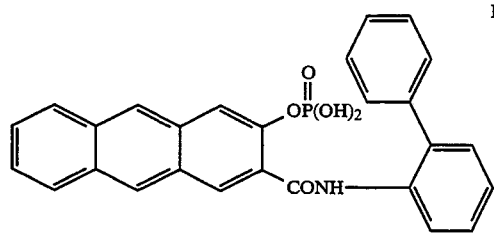

Formula 9

EXAMPLES 2-8

Figure 2:
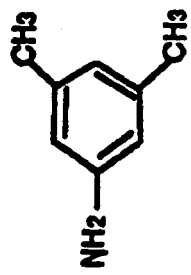

In examples 2-8, various types of anilines were used to obtain anthracene derivative phosphates in the same way as Example 1. FIGS. 1-3 show each aniline and the description of resultant anthracene derivative phosphate in Example 2-8, respectively.

In order to prove the usefulness of anthracene derivative phosphate as a nucleic acid probe, DNA detection was executed on a nylon membrane by using DNA Labeling and Detection Kit (produced by Boehringer Mannheum Co.), and 3-hydroxy-2-anthracenecarboxamide-2-phenylanilide as the anthracene derivative phosphate.

Figure 4:
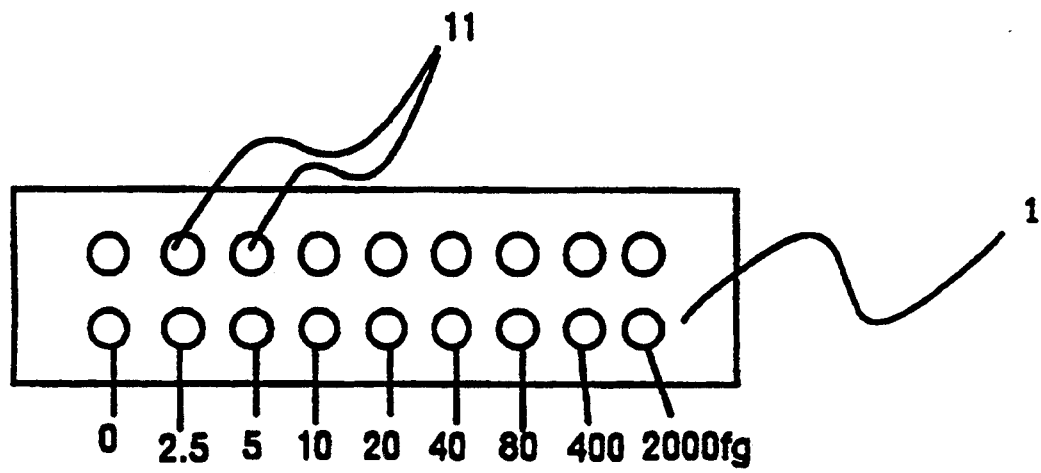
FIG. 4 shows a nylon membrane filter used for DNA detection tests.

The lambda DNA was labeled by Digoxigenin (Dig.) to be diluted to 0 fg, 2.5 fg, 5 fg, 10 fg, 20 fg, 40 fg, 80 fg, 400 fg, and 2 pg, respectively. As FIG. 4 shows, each of the diluted solution was spotted onto the nylon membrane filter. Those spots were heated to 80° C. for 30 minutes under pressure to be immobilized.

In this experiment, every spot included 100 ng ($100 \times 10^{-9}$ g) DNA of herring sperm as non-idiosyncratic DNA. In FIG. 4, the reference numeral 1 designates the nylon membrane filter, and reference numeral 11 designates spots of the nucleic acid sample.

The nylon membrane filter was subjected to blocking processing. It was reacted with the Dig antibody of labeled alkaline phosphatase to remove the unreacted antibody. For the reaction purpose, 3-hydroxy-2-anthracenecarboxamide-2-phenylanilide phosphate (obtained in Example 1) in final concentration of 200 μg/ml was reacted in the solution of 100 mM Tris(PH9.5), 100 mMNaCl, and 50 m MgCl2.

The fluorescent signal was detected by taking the picture thereof with Polaroid film (trademark) under the source of ultraviolet excited light.

TABLE 1 shows the results of evaluating tests, where "+" represents "detectable" and "−" represents "not detectable". The TABLE shows that even a very small amount of the sample, for example, 10 fg, was detectable with the aid of 3-hydroxy-2-anthracenecarboxamide-2-phenylanilide phosphate. It was, thus, proved to be very effective as a probe for detecting nucleic acid.

Each anthracene derivative phosphate of Examples 2-8 was subjected to the same test as described above. The respective results are also shown in TABLE 1. All the anthracene derivative phospates obtained according to the present invention were proved to be effective and useful as a probe for detecting nucleic acid.

While the invention has been described with reference to examples, it is to be understood that modifications or variations may be easily made by a person of ordinary skill in the art without departing form the scope of the invention which is defined by the appended claims.

TABLE 1

| | Detection sensitivity 1 fg = $10^{-15}$ g (Labeled DNAfg) | | | | | | | | |
|---|---|---|---|---|---|---|---|---|---|
| Examples | 0 | 2.5 | 5 | 10 | 20 | 40 | 80 | 400 | 2000 |
| 1 | − | − | − | + | + | + | + | + | + |
| 2 | − | − | − | + | + | + | + | + | + |
| 3 | − | − | − | − | − | − | + | + | + |
| 4 | − | − | − | − | − | − | − | − | + |
| 5 | − | − | − | − | − | − | + | + | + |
| 6 | − | − | − | − | − | − | − | + | + |
| 7 | − | − | − | − | − | − | − | − | + |
| 8 | − | − | − | − | − | − | − | − | + |

What is claimed is:

1. A method of detecting nucleic acids, proteins and other chemical compounds which comprises the steps of:

binding said nucleic acids, proteins, and other chemical compounds to a phosphatase, reacting said phosphatase wherein said binding does not affect the catalytic activity of said phosphatase, bound with an anthracene derivative phosphate having the formula where "R" is a substituent bound to a phenyl group which is in turn bound to the N of the amide group, irradiating the reaction produce with excited light; and detecting the emitted fluorescence;

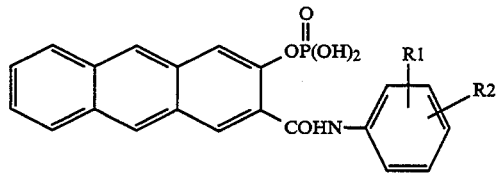

where R1 and optional R2 are selected from the group consisting of hydrogen, alkyl, alkoxyl, phenyl, and diphenyl, and are bound to a phenyl group which is in turn bound to the N of the amide group, to form a dephosphorylated anthracene derivative reaction product, irradiation said reaction produce with ultraviolet light, and detecting emitted fluorescence, wherein the emission of fluorescence is indicitave of the presence of said nucleic acids, proteins, and other chemical compounds.

2. The method as in claim 1, wherein R1 but not optional R2 is present, and wherein said R1 is bound to the C2 of said phenyl group.

3. The method as in claim 1, wherein both R1 and R2 are present, and wherein said R1 and R2 are bound to the $C_2$ and $C_4$ of said phenyl group.

4. The method as in any one of claims 1, 2 or 3, wherein said anthracene derivative phosphate is selected from the group consisting of: 3-Hydroxy-N-2'-methylphenyl-2-anthracenecarboxamide phosphate, 3-Hydroxy-N-2',4'-dimethylphenyl-2-anthracenecarboxamide phosphate, 3-Hydroxy-N-2'-methoxyphenyl-2-anthracenecarboxamide phosphate, 3-Hydroxy-N-2',4'-dimethoxyphenyl-2-anthracenecarboxamide phosphate, 3-Hydroxy-N-2'-biphenyl-2-anthracenecarboxamide phosphate.

* * * * *